US006297943B1

(12) United States Patent
Carson

(10) Patent No.: US 6,297,943 B1
(45) Date of Patent: Oct. 2, 2001

(54) CAPACITOR WITH THERMOSEALED POLYMERIC CASE FOR IMPLANTABLE MEDICAL DEVICE

(75) Inventor: Dean F. Carson, Mountain View, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 09/272,902

(22) Filed: Mar. 19, 1999

(51) Int. Cl.[7] .................................................... H01G 9/00
(52) U.S. Cl. .......................... 361/500; 361/302; 361/520; 361/308; 361/538; 29/25.42; 607/5; 607/4
(58) Field of Search ..................................... 361/500, 302, 361/520, 538, 301.4, 329, 508, 528; 607/5, 4; 29/25.42

(56) References Cited

U.S. PATENT DOCUMENTS

| 4,009,285 | * | 2/1977 | Spooner | 426/8 |
|---|---|---|---|---|
| 4,180,073 | * | 12/1979 | Michaels | 128/260 |
| 4,748,094 | * | 5/1988 | Howard et al. | 429/90 |
| 5,131,388 | * | 7/1992 | Pless et al. | 128/419 |
| 5,370,663 | * | 12/1994 | Lin | 607/5 |
| 5,522,851 | | 6/1996 | Fayram | 607/7 |
| 5,814,082 | * | 9/1998 | Fayram et al. | 607/5 |
| 5,926,357 | * | 7/1999 | Elias et al. | 361/302 |
| 5,983,472 | * | 11/1999 | Fayram et al. | 29/25.42 |

* cited by examiner

*Primary Examiner*—Dean A. Reichard
*Assistant Examiner*—Nguyen T Ha
(74) *Attorney, Agent, or Firm*—Steven M. Mitchell

(57) ABSTRACT

An electrolytic capacitor with a polymeric housing in the form of a pocket defining a chamber, with an opening along a selected edge. The opening has opposed sides that are sealed together to provide a seam. A number of conductive layers are positioned within the chamber, and a feed-through conductor element has a first end electrically connected to the layers. An intermediate portion of the feed through passes through the seam, and an external portion extends from the housing. The housing may be vacuum formed high density polyethylene, with the feed-through contained in an elastomeric sleeve having a flattened cross section to be readily received in the seam, and to accommodate thermal expansion differences between the housing and the feedthrough. The device may be manufactured by inserting a stack of layers in the pocket, and thermally welding across the opening of the pocket on a single weld line.

8 Claims, 6 Drawing Sheets

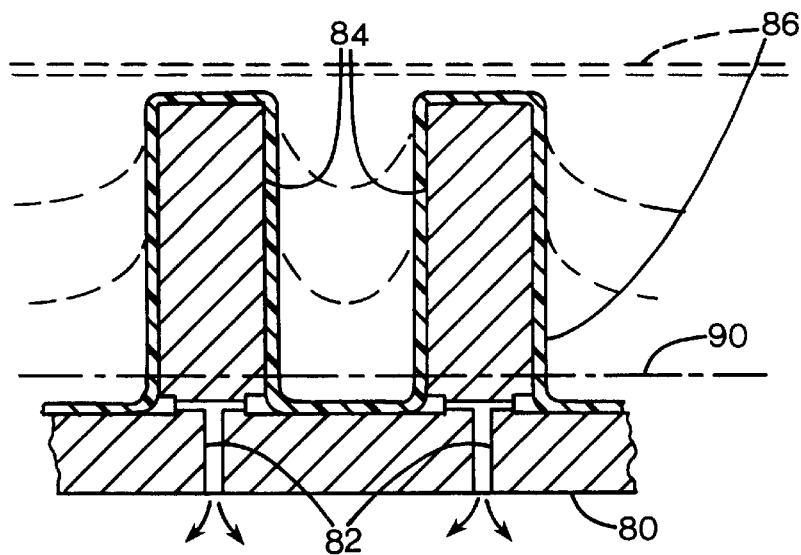
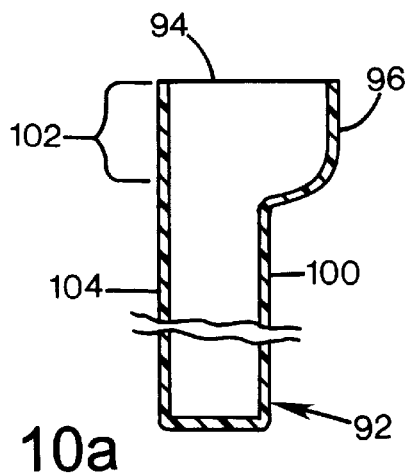
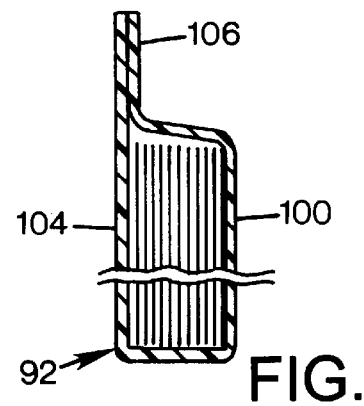
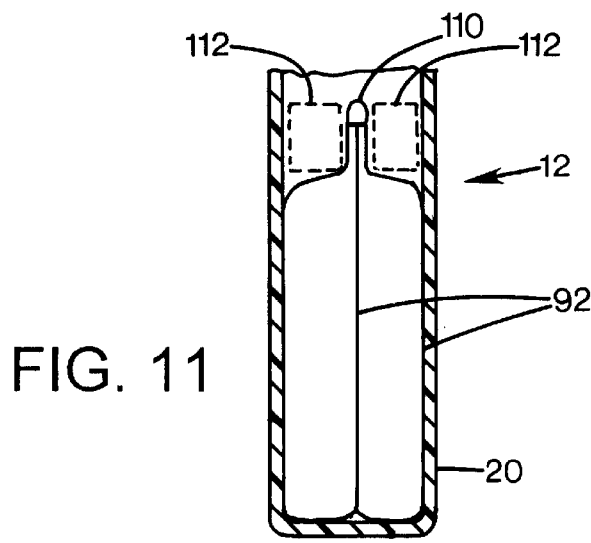

US 6,297,943 B1

CAPACITOR WITH THERMOSEALED POLYMERIC CASE FOR IMPLANTABLE MEDICAL DEVICE

FIELD OF THE INVENTION

This invention relates to electronic components for implantable medical devices, and more particularly to charge storage components for cardiac stimulation devices.

BACKGROUND OF THE INVENTION

Defibrillators are implanted in patients susceptible to cardiac arrhythmias or fibrillation. Such devices provide cardioversion or defibrillation by delivering a high voltage shock to the patient's heart, typically about 500–750V. High voltage capacitors are used in defibrillators to accumulate the high voltage charge following detection of a tachyarrhythmia. In the effort to make implantable devices as small and thin as possible, flat aluminum electrolytic capacitors are used.

Such a flat capacitor is disclosed in U.S. Pat. No. 5,131, 388 to Pless et al., which is incorporated herein by reference. Flat capacitors include a plurality of aluminum layers laminarly arranged in a stack. Each layer includes an anode and a cathode, with all of the anode layers and all of the cathode layers being commonly connected to respective connectors. The layers may be cut in nearly any shape, to fit within a similarly shaped aluminum housing designed for a particular application. Normally, the cathode layers are together connected to the housing, while the anodes are together connected to a feed-through post that tightly passes through a hole in the housing, but which is electrically insulated from the housing. The feed-through post serves as an external connector for interfacing with other components.

Flat capacitors may be provided with polymeric housings that eliminate the need for additional insulating layers to insulate conductive layers from the housing, reducing total size and increasing energy density (measured in Joules/cc). Such a housing is disclosed in U.S. patent application Ser. No. 09/130,812, filed Aug. 7, 1998, by inventor D. Carson, which is incorporated herein by reference. This device uses an injection molded two-part plastic "dish-and lid" housing that is ultrasonically welded about its periphery. Electrical feedthrough wires pass from the interior to the exterior through holes provided at the weld line. While effective, this housing requires sidewalls that are wide enough to include mating grooves and ridges for ultrasonic welding. In addition, injection molding requires more than a minimum wall thickness for the major panels to allow molten plastic material to flow through the mold. These thicknesses add to the total capacitor volume, decreasing the energy density from what would otherwise be ideal. In addition, the ultrasonic welding process may be sensitive to out-of-tolerance part dimensions, and requires significant operator care and skill, adding to manufacturing costs.

SUMMARY OF THE INVENTION

The disclosed embodiment overcomes the limitations of the prior art by providing an electrolytic capacitor with a polymeric housing in the form of a pocket defining a chamber, with an opening along a selected edge. The opening has opposed sides that are sealed together to provide a seam. A number of conductive layers are positioned within the chamber, and a feed-through conductor element has a first end electrically connected to the layers. An intermediate portion of the feed through passes through the seam, and an external portion extends from the housing. The housing may be vacuum-formed high density polyethylene, with the feed through contained in an elastomeric sleeve having a flattened cross section to be readily received in the seam, and to accommodate thermal expansion differences between the housing and the feedthrough. The device may be manufactured by inserting a stack of layers in the pocket, and thermally welding across the opening of the pocket on a single weld line.

BRIEF DESCRIPTION OF THE DRAWINGS

FIG. 9 is sectional side view of a capacitor housing according to the embodiment of FIG. 1 in an intermediate stage of manufacturing.

FIGS. 10a and 10b are sectional side views of a capacitor at different stages of manufacturing according to an alternative embodiment of the invention.

FIG. 11 is a sectional side view of a defibrillator including a pair of capacitors according to the embodiment of FIGS. 10a and 10b.

DETAILED DESCRIPTION OF A PREFERRED EMBODIMENT

Figure 1:
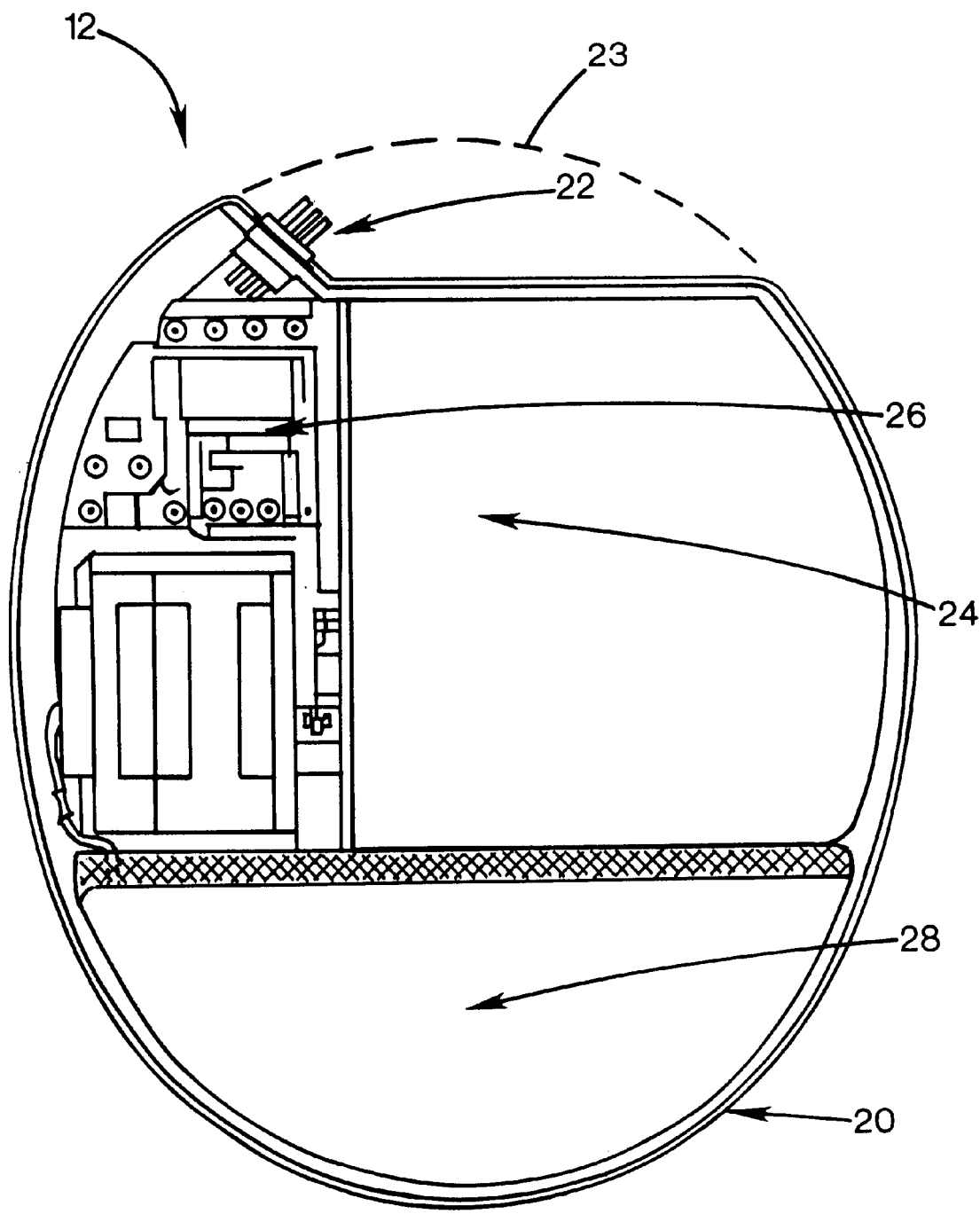
FIG. 1 is a plan view of an implantable defibrillator according to a preferred embodiment of the invention.

FIG. 1 illustrates a defibrillator 12 for pectoral implantation, with a portion of the housing removed to show interior components. The defibrillator includes an outer housing 20 that includes a lead set feed-through connector 22 for attachment of an endocardial lead set in a header 23. The housing 20 contains a battery cell 24, electronic circuitry 26, and a capacitor 28. The battery provides low voltage electrical energy to a transformer in the circuitry to charge the capacitors so that they may provide a high voltage shock when needed. The circuitry 26 connects to the lead connector so that it may sense and analyze electrical signals from the heart, and control the delivery of an appropriate therapy such as a high voltage shock.

Figure 2:
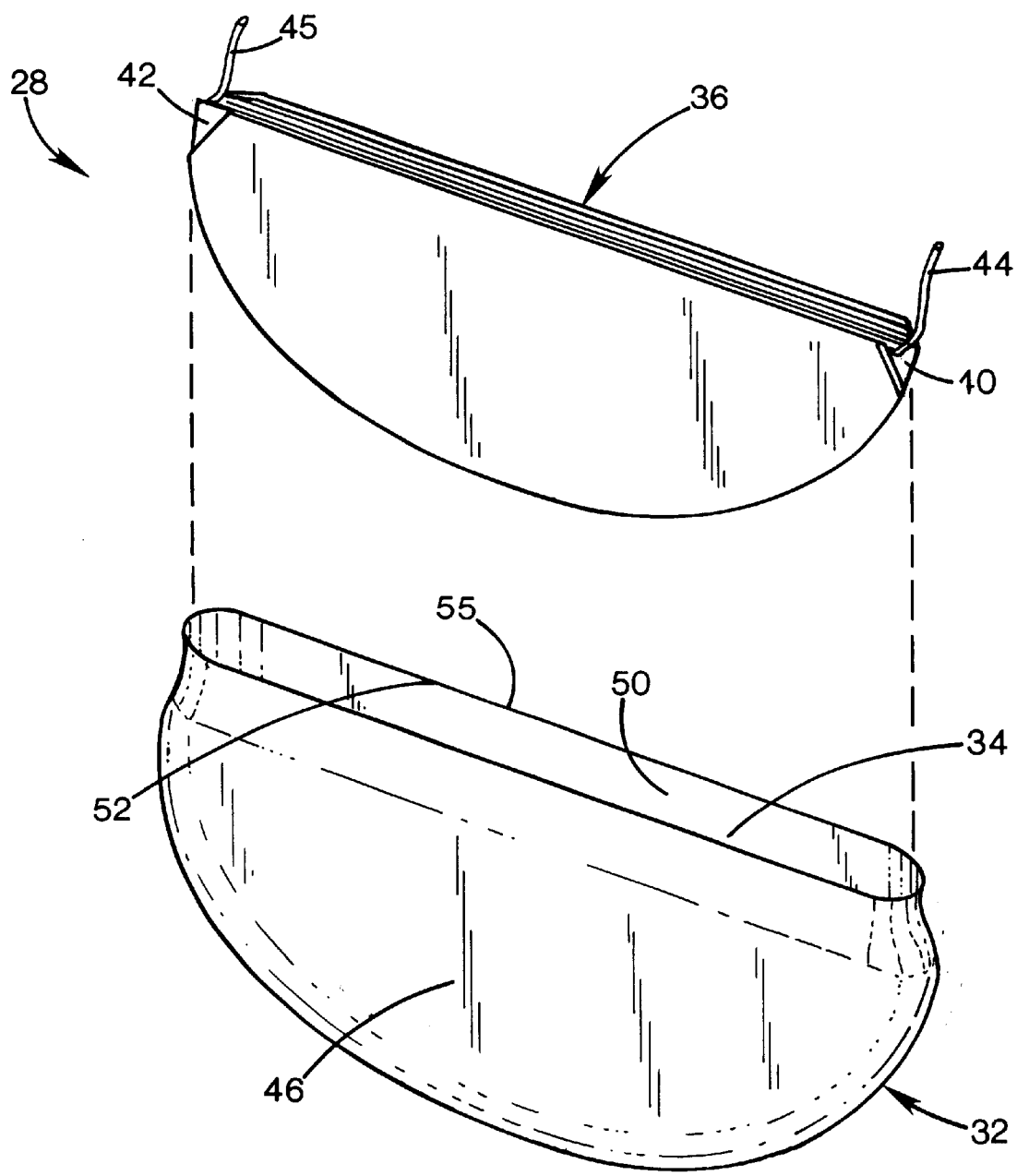
FIG. 2 is an exploded view of a capacitor according to the embodiment of FIG. 1.

FIG. 2 illustrates an exploded view of the capacitor 28, which may be designed as virtually any flat shape to conform to a desired housing shape. In the preferred embodiment, it is crescent-shaped to conform to a compact, ellipsoidal outer device housing. The capacitor includes a plastic housing 32 defining a chamber 34, in which resides a capacitor stack 36.

The capacitor stack 36 is formed of a number of alternating interleaved cathode sheets and anode sheets with separator sheets therebetween. A liquid electrolyte is introduced into the stack and impregnates the separator sheets. The anode sheets include anode tabs 40 extending in registration with each other beyond the cathode sheets and separator sheets at one end of the stack 36. Similarly, the cathode sheets include cathode tabs 42 extending beyond the anode sheets and registered for connection to each other. The cathodes, like the anodes, are connected together in parallel when the respective tabs are brought together in a bundle. To provide electrical contact to the anodes, a flexible aluminum anode feed-through wire 44 is connected to the anode tabs 40 and extends away from the stack and out of the housing. A cathode feed-through wire 45 similarly extends from the cathode tabs.

The housing 32 is essentially a flat pocket formed of a seamless sheet, with opposed major flat sides 46, 50, and a single opening 52 along a straight edge of the pocket. Preferably, the housing is formed by vacuum forming of a polyolefin sheet such as high density polyethylene, or any other suitable thermoformable material. This high density material provides mechanical strength and electrical insulation. The wall thickness may be between 2–20 mils, although 5–10 mils is preferred. With the vacuum forming process described below, the wall thickness will tend to vary over a single part formed from a flat sheet of constant thickness. The housing 32 is sized to closely receive the capacitor stack, with the stack occupying the chamber fully, except at the opening 52.

Figure 3:
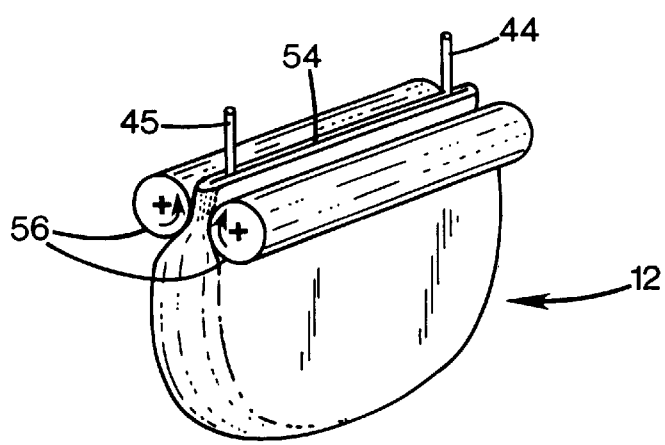
FIG. 3 is an perspective view of a capacitor according to the embodiment of FIG. 1 in an intermediate stage of manufacturing.

As shown in FIG. 3, the stack is installed in the housing with the feed wires 44, 45 extending from the opening 52, which has been compressed together to form a seam 54 running along all or most of the edge 55. A pair of compression rollers 56 compresses together the housing sides at the edge, capturing the feed-through wires 44, 45. The rollers rotate to draw the housing into their nip until all possible space in the chamber is eliminated. Heat is applied to weld together the seam to provide a seal. Heating may be provided by an air or radiant heat source, or by heat conducted from heated rollers or other bar heater. In alternative embodiments, ultrasonic welding or adhesive bonding, or solvent welding may be employed.

Figure 4:
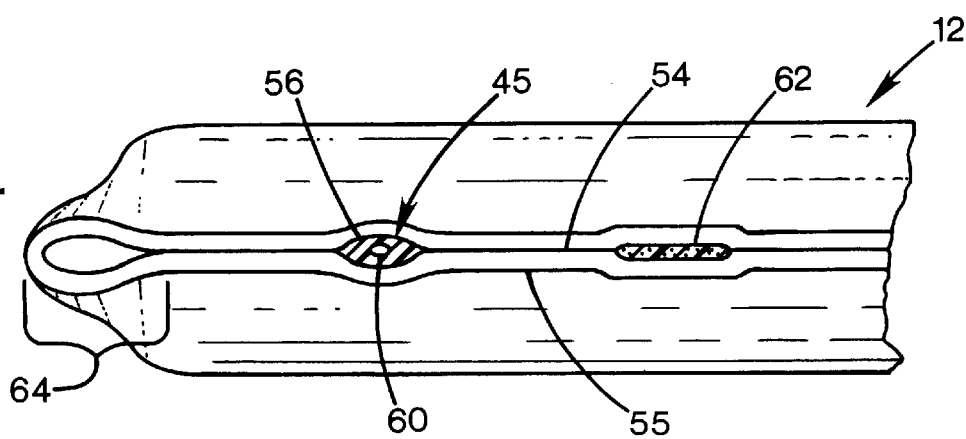
FIG. 4 is an enlarged edge view of a capacitor according to the embodiment of FIG. 1.

FIG. 4 shows the edge 55 of the capacitor housing, with the feed-through wire 45 captured in the seam 54. The wire has an elastomeric sleeve 56 surrounding an aluminum conductor 60. The sleeve has a lenticular cross section having an acute vertex along opposed edges. These vertices allow the housing material to smoothly conform to the sleeve, without any voids where the seam line meets the sleeve. The elastomeric sleeve is preferably formed of EPDM or similar olefenic elastomer having compatible properties with the housing material to form an adequate bond. Thus, the EPDM sleeve thermally bonds to the housing material. The EPDM is further advantageous in this application in that it is a thermoset material which will not melt or change shape or thickness during bonding. To provide a positive seal between the wire 60 and the sleeve 56, the wire may have a larger diameter than the sleeve bore, maintaining compressive contact.

The sleeve material not only provides a positive bond with the heated housing material, but its flexible properties accommodate any thermal expansion differences between the plastic housing and the aluminum wire. Where such expansion differences are not of concern, the feed-through may be an all aluminum conductor having a flat shape, such as a foil strip, or a drawn wire having the lenticular profile shown. A further advantage of the illustrated wire shape is that the broad surfaces are less prone to penetrate or rupture through the thin housing wall during compressive heating, as might a small circular wire.

FIG. 4 further shows a vent element 62 welded into the seam 54. This is a strip of porous material that extends into the chamber, and which has an edge exposed to the environment, allowing gas generated or trapped in the chamber to slowly escape, while containing fluid within the chamber. In the preferred embodiment, the vent is a strip of PTFE felt that is sufficiently hydrophobic that it does not wick the typically hydrophilic electrolyte, and which has an adequately high melting point that it is unaffected by temperatures used to seal the housing. Alternative vents include sintered PTFE or ultra-high molecular weight polyethylene (UHMWPE). Such a porous vent is preferred over diffusion membranes or plugs such as might be formed of PDMS silicone, because during vacuum cycles used for evacuation of gas, as well as gas generated during electrical testing, diffusion barriers do not relieve pressure quickly enough, and the housing would expand undesirably. Even if the vent strip material does not form a bond with the housing material during welding, the texture of the strip admits adequate housing material to form a mechanically engaged connection adequate to prevent fluid leakage.

FIG. 4 also shows that at one end of the seam, an open portion 64 of the seal is left unsealed. This is a temporary aperture that will later be sealed, but which provides a ready exit for excess trapped air during sealing, and an inlet for electrolyte injection following initial sealing. While it may be possible to pre-saturate the stack with electrolyte prior to insertion and sealing, it is believed that this may impair the sealing process, and may generate unwanted vaporization from the heat of sealing. Accordingly, in the preferred embodiment, the housing is mostly sealed after stack insertion, then electrolyte is added (preferably under a vacuum), and the remaining open portion is sealed, so that little or no air occupies the chamber.

Figure 5:
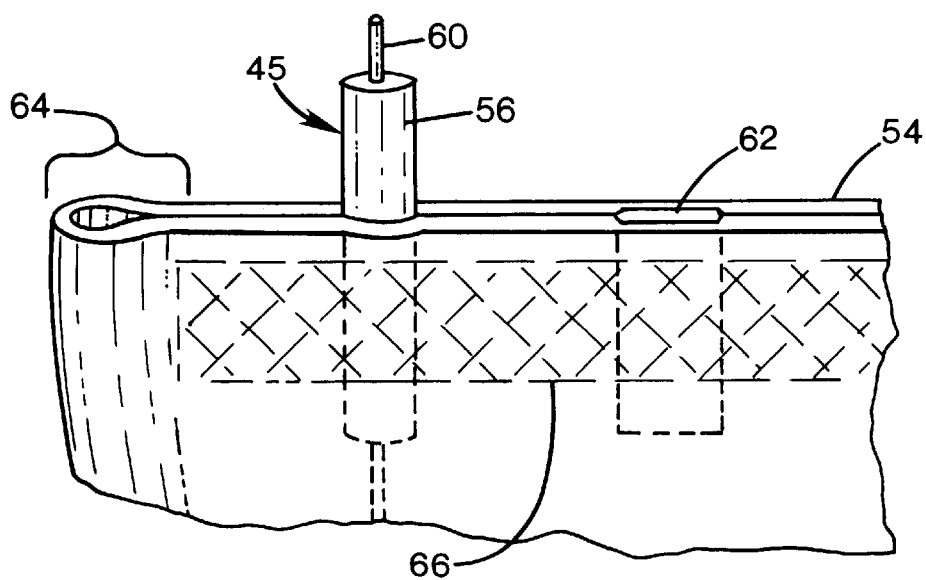
FIG. 5 is an enlarged perspective view of a capacitor according to the embodiment of FIG. 1.

As shown in FIG. 5, the open portion 64 of the seam is away from the end of a sealing region 66 that extends across the remainder of the edge, including beyond the opposite end of the seam. The sleeve 56 of the wire need only cover an intermediate portion passing through the sealing region, as the vent element need only extend just beyond the sealing region to the interior and exterior of the housing.

Figure 6A:
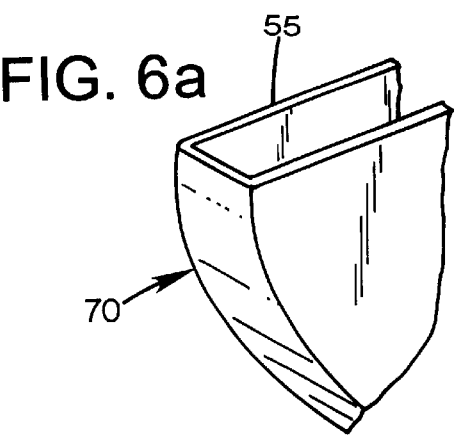
FIGS. 6a–8b are perspective views of alternative capacitor housings in open and sealed configurations.
Figure 6B:
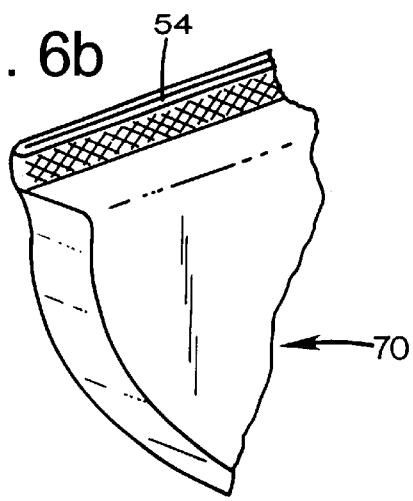
Figure 7A:
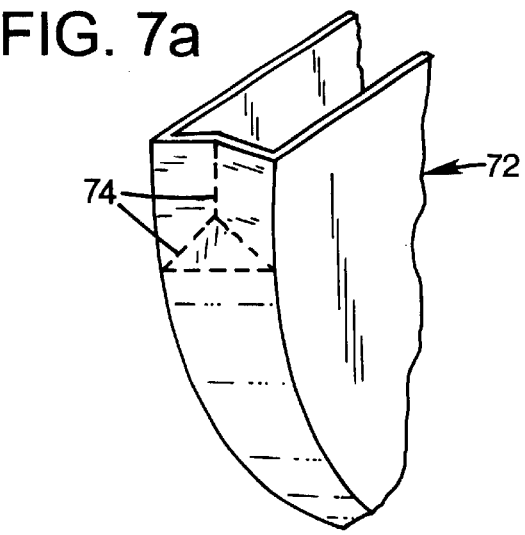
Figure 7B:
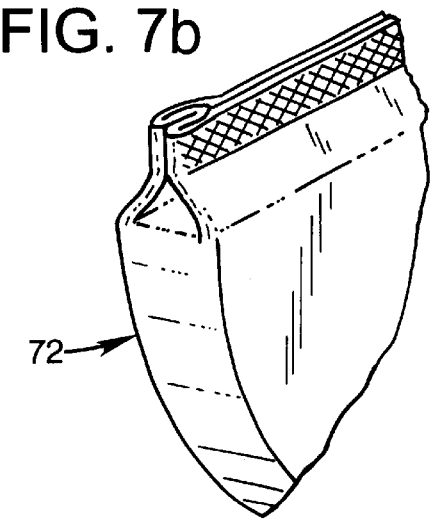
Figure 8A:
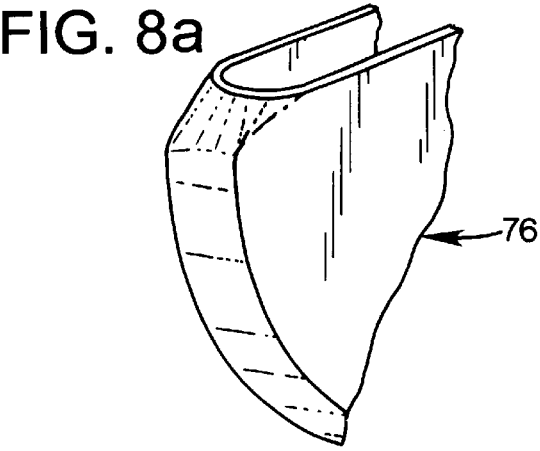
Figure 8B:
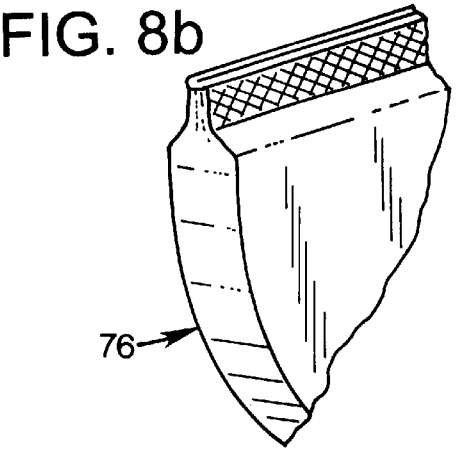

FIG. 6a shows an alternative housing 70 having a simple open end with straight walls at the open edge 55. When sealed as shown in FIG. 6b, the end of the seam extends beyond the end of the rest of the housing, as the end wall of the housing at the edge is folded outward. Where this protrusion is unwanted, an alternative housing 72 shown in FIG. 7a may be provided with score lines 74 in a pattern that causes the end panel to fold inward, as shown in FIG. 7b. This gable-end technique ensures that there are no protrusions beyond the housing ends, and requires a sealing process capable of accommodating the thicker end portion of the seams. A further alternative housing 76 is shown in FIGS. 8a and 8b. The housing opening is essentially pursed at the ends of the opening, so that the opening is shorter than the rest of the housing. When this opening is flattened and sealed, the lengthening that naturally occurs remains at or less than the length of the housing, avoiding protruding seam portions.

FIG. 9 shows the vacuum forming process used to produce the housing. A vacuum table 80 has vent holes 82 beneath each of an array of positive forms 84 that correspond to the interior shape of the housing. A heated sheet 86 of the housing material is placed above the forms, and is sealed to the edges of the vacuum table (in a manner not shown) to prevent air from being admitted between the sheet and the table. A vacuum is drawn from beneath the sheet through vents 82, and the sheet is conformed to the forms. After the sheet cools adequately, it is removed, and the housings are individuated by cutting along cutting line 90. By using male forms, the material stretching is least at the upper or peripheral edge, while material thins more significantly over the major faces of each housing, more so near the open ends. This provides structural strength at the edge walls, but reduced thickness over the large areas, providing a greater effect on volume reduction. These thin major walls are readily made by vacuum forming, while an injection molding process would have the greatest difficulty with a small thickness over a large area. Where it is necessary to avoid excessively thin or thick regions, the sheet may be pre-molded to provide increased or reduced thickness to compensate as needed.

FIGS. 10a and 10b show an alternative housing configuration 92 having an opening 94 with an upper wall portion 96 extending well beyond the major surface 100 from which it upstands. An opposed wall portion 102 is co planar with the opposed major surface 104. During sealing, the first wall portion is folded across to meet the unmoved portion 102, so that the seam 106 extends in the plane of the major surface 104. As shown in FIG. 11, two such capacitors may be connected back to back and installed in the capacitor housing, so that the seams are adjacent. This allows simple electrical connection of the capacitors by conductor 110, and provides usable volumes 112 adjacent the seam and contiguous with the rest of the device volume for occupation by other circuitry. Alternatively, the seams may be placed against opposite walls of the housing, and the space between efficiently occupied by circuitry to reduce overall device volume.

Figure 12:
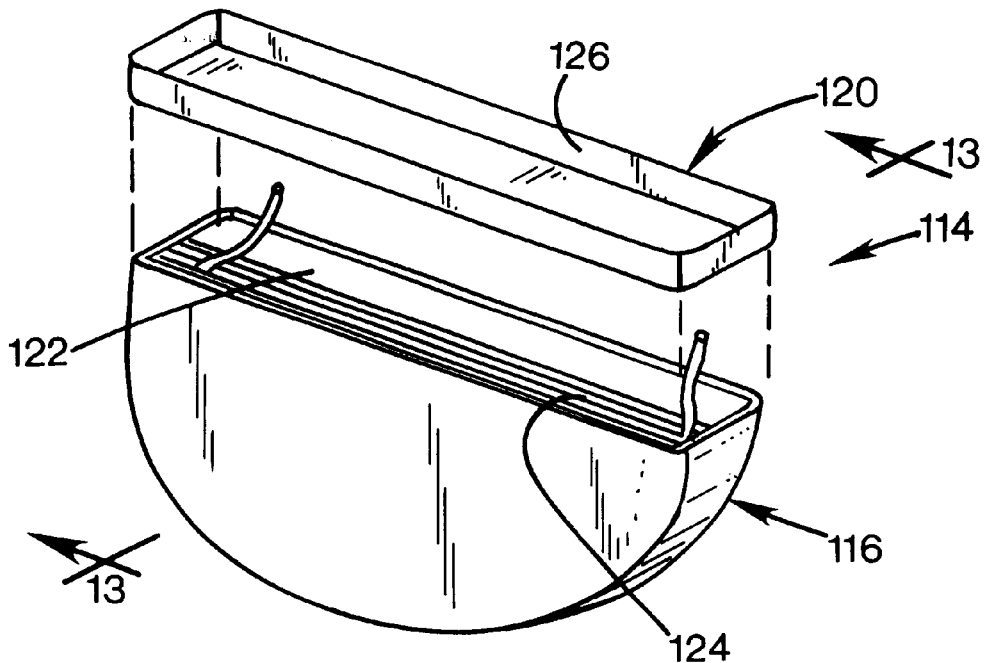
FIG. 12 is an exploded view of a capacitor according to an alternative embodiment of the invention.
Figure 13:
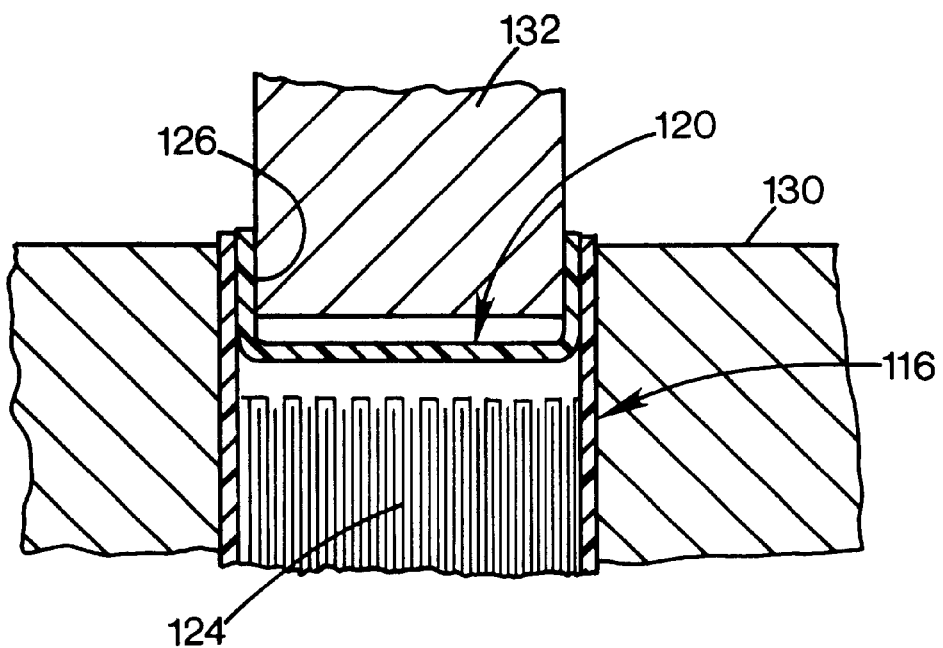
FIG. 13 is an enlarged side view of a capacitor according to the embodiment of FIG. 12, in an intermediate stage of manufacturing.

FIG. 12 shows an alternative housing configuration 114 having a pocket-type housing 116, but with a separate lid 120. The lid is sized to fit the opening 122 along the straight edge of the housing, and to be sealed about the periphery of the opening. This alternative does not require folding of the housing edge, which may be straight as it extends beyond the inserted capacitor stack 124. The lid 120 has a planar body that fills the opening, and an upstanding peripheral flange 126. As shown in FIG. 13, the lid is installed so that the body is nearly touching the edge of the stack 124, with the flanges 126 terminating at the edges of the housing walls. The device is inserted into a die 130 having a pocket sized to closely receive the capacitor, and a tool 132 is inserted into the space defined by the flange of the lid. With the lid firmly positioned, any of the sealing methods noted above may be applied, including radiant, convective, or conductive heat, as well as ultrasonic energy, adhesive, or solvent welding. The lead wires may be welded into the seams as discussed above. In an alternative embodiment, instead of the vacuum formed lid shown, a molded plastic lid may be provided. Such a lid may have more precise detailed features, such as apertures that accept feed-through wires.

Although the above invention is described in terms of a preferred embodiment, the invention is not intended to be so limited.

What is claimed is:

1. An electrolytic capacitor comprising:

a polymeric housing comprising a pocket defining a chamber and having an opening along a selected edge;

the opening comprising opposed sides sealed together to provide a scam;

a plurality of conductive layers positioned within the chamber; and a feed-through conductor element having a first end electrically connected to the conductive layers, an intermediate portion passing through the seam, and an external portion extending from the housing.

2. The capacitor of claim 1 wherein at least the intermediate portion of the feedthrough includes a surrounding sleeve, and wherein the sleeve material is different from the conductive feedthrough material.

3. The capacitor of claim 2 wherein the sleeve has an elongated cross section at the intermediate portion.

4. The capacitor of claim 2 wherein the sleeve is an elastomeric material.

5. The capacitor of claim 1 wherein the housing is formed of high density polyethylene.

6. The capacitor of claim 1 wherein the seam is a single line.

7. The capacitor of claim 1 including a vent element captured within the seam.

8. The capacitor of claim 1 including a second separate feed-through element.

* * * * *